United States Patent [19]

Hofmann et al.

[11] 4,400,568

[45] Aug. 23, 1983

[54] PROCESS FOR PREPARING STYRENE, AND AN APPROPRIATE AGENT

[75] Inventors: Hanns Hofmann; Gerd Emig, both of D-8520 Erlangen; Wolfgang Ruppert, D-6104 Seeheim, all of Fed. Rep. of Germany

[73] Assignees: Hanns Hofmann; Gerd Emig, both of Erlangen; Wolfgang Ruppert, Seeheim, all of Fed. Rep. of Germany

[21] Appl. No.: 368,920

[22] Filed: Apr. 16, 1982

[51] Int. Cl.³ ............................................. C07C 5/36
[52] U.S. Cl. .................................. 585/443; 252/437; 585/444; 585/440
[58] Field of Search ............... 585/440, 441, 443, 445, 585/444; 252/437, 469

[56] References Cited

U.S. PATENT DOCUMENTS

| | | | |
|---|---|---|---|
| 3,416,884 | 12/1968 | Stynes et al. | 252/437 |
| 4,059,679 | 11/1977 | Clearfield | 252/437 |
| 4,291,184 | 9/1981 | Crum et al. | 585/443 |

FOREIGN PATENT DOCUMENTS 45-4041182  5/1970  Japan ................................ 585/443

OTHER PUBLICATIONS

Clearfield et al., J. Inorg. Nucl. Chem., 26, 117 (1964); 30 2249 (1968).
Clearfield et al., J. Catalysis, 51 431–434 (1978).
Hattori et al., J. Inorg. Nucl. Chem., 40 1107–1111 (1978).
Hattori et al., J. Catalysis, 56, 294–295 (1979).
Clearfield et al., J. Inorg. Nucl. Chem., 37, 1283–1290 (1975).

*Primary Examiner*—Delbert E. Gantz
*Assistant Examiner*—A. Pal
*Attorney, Agent, or Firm*—Curtis, Morris & Safford

[57] ABSTRACT

The invention relates to a process for oxidatively dehydrogenating dehydrogenatable organic compounds to prepare styrene. In this process, the compounds mentioned are reacted in the vapor phase with oxygen at a temperature above 350° C. in the presence of a catalyst based on zirconium phosphate. Suitable dehydrogenatable organic compounds are above all saturated alkylaromatics, in particular ethylbenzene.

14 Claims, No Drawings

PROCESS FOR PREPARING STYRENE, AND AN APPROPRIATE AGENT

The invention relates in the first place to a process for oxidatively dehydrogenating dehydrogenatable organic compounds to prepare styrene.

A known process which involves the thermal dehyrogenation of ethylbenzene (EB) as an equilibrium reaction affords conversions of EB of only 35–40% while the styrene selectivities are high at 85–95% [E. D. Hausmann and C. J. Kiwo, Ind. Eng. Chem., Fundamentals 5 295 (1966)]. The oxidative dehydrogenation of EB to give styrene as an alternative process to thermal dehydrogenation was initially only successful when using promoters such as $SO_2$ [G. S. Schaffel and R. L. Marcell, paper presented at the 71st AICHE Meeting, Dallas, Texas, February 20–23, 1972], $H_2S$ [M. Vadekar, J. S. Pasternak and N. J. Gaspar, Can. J. Chem. Eng. 52 (1974) 788] and halogens such as $I_2$ [J. H. Raley, R. D. Mullineaux and C. W. Bittner, J. Am. Chem. Soc., 85 3174 (1963)]. The use of oxygen as sole oxidation agent and of known catalysts [C. R. Adams, H. H. Voge, C. Z. Morgan and W. E. Armstrong, J. Catalysis 3 379 (1964)] led to uncontrolled combustion and cracking reactions.

Although the use of alkaline earth/nickel phosphate catalysts, as described in U.S. Pat. No. 3,953,126, produced high conversions and selectivities for the reaction with $O_2$ as sole oxidation agent, the space-time yield of styrene was only moderate.

In contrast, the object of the invention is to achieve a higher space-time yield of styrene (relative to the amount of catalyst used) and to produce chiefly CO and $CO_2$ as by-products.

This object is achieved by reacting dehydrogenatable organic compounds in the vapor phase with oxygen at a temperature above 350° C. in the presence of a new catalyst based on zirconium phosphate. In this reaction oxygen is used as sole oxidation agent. Suitable dehydrogenatable organic compounds are saturated alkylaromatics, above all ethylbenzene, but also, for example, diethylbenzene or ethylnaphthalene. The catalyst used is preferably zirconium phosphate which has been treated with orthophosphoric acid. The catalyst has a zeolite structure and the properties of an inorganic ion exchange material. It therefore preferably also contains exchanged ions of the groups Ia, IIa, IVb, Vb, VIb, VIIb and VIII of the periodic system of the elements, namely generally in a concentration of 1–20% by weight. Suitable examples are the K, Cs, Mg, Ba, Cr, Mn, Fe and Ni ions, in particular K, Cs, Ba, Fe or Ni ions.

Conversion and selectivity are particularly favorable when a mixture of an oxygen-containing gas and a dehydrogenatable compound, with or without dilution by an inert substance, in the dilution case the ratio of the diluent to the dehydrogenatable compound being at most 10/1, is passed over the zirconium phosphate catalyst at temperatures of 350° C.–550° C. and residence times of 0.5 to 5, preferably 0.7 to 3.2, in particular 1.0–1.8, grams of gas mixture per gram of catalyst per hour. The dehydrogenatable organic compound preferably used is ethylbenzene, in which case the temperature range is from about 380° C. to 530° C.

The invention also relates to an agent for carrying out the above mentioned process, in the form of a zirconium phosphate catalyst as described above.

Zirconium phosphate is prepared, for example, by the method described by Clearfield and Stynes in *J. Inorg. Nucl. Chem.* 26 117 (1964).

In this method, a gel-like amorphous precipitate is first obtained by adding an excess of phosphoric acid or of a soluble phosphate to a soluble zirconium salt. This can be carried out, for example, by mixing an 0.5 M zirconium (IV) dichloride oxide solution with a 3 M orthophosphoric acid in a ratio which is such that the atomic ratio of zirconium to phosphorus is 1:2.

This precipitate is then converted into a crystalline form, namely by impregnating the gel-like precipitate with an at least 10 M, preferably 10–15 M, orthophosphoric acid; preferably by adding an excess, at least 1 liter, or orthophosphoric acid of the abovementioned concentration to each 100 g of the gel-like precipitate and maintaining the resulting mixture for 10 to 14 hours, with stirring, at temperatures around the boiling point. The impregnating step is completed by then leaving the precipitate to stand in the orthophosphoric acid for 30 to 40 hours.

The catalyst preferably has a surface area of 10–50 $m^2/g$, in particular of 25–40 $m^2/g$. This surface area can be obtained by establishing a suitable acid strength (at least 10 M) and a sufficiently strong turbulence in the impregnating vessel.

The resulting crystalline zirconium phosphate is filtered off from excess phosphoric acid and then washed with water until the water draining off has a pH of 2–3.

The zirconium phosphate is dried in air at temperatures between 120° C. and 250° C., preferably between 120° C. and 200° C., for a period of 24–48 hours.

The ratio of $PO_4$ to Zr becomes established in the preparative method described above at values between 2 and 3. The favorable incorporation mentioned of additional metal ions is effected by ion exchange in which the zirconium phosphate catalyst, after the drying step, is stirred for 50 to 80 hours in a corresponding metal salt solution.

Because of their size, Cs ions can be incorporated into the crystal latice only by adding a corresponding solution before the impregnation with orthophosphoric acid and the drying. For example, a 1 N solution of CsCl is added to the gel-like zirconium phosphate precipitate and 12 M orthophosphoric acid is then added for the impregnation. The other steps in the procedure thereafter correspond to those used in the preparation of undoped crystalline zirconium phosphate.

The dried product is comminuted and either pelletized or classified by screening.

The process according to the invention is distinguished by the following process data.

The molar ratio of oxygen to alkylaromatics can be 0.5–2 moles of $O_2$ per mole of alkylaromatic, the preferable range being 0.7 to 1.5, in particular 0.9–1.2, moles of $O_2$ per mole of alkylaromatic. The oxygen can be pure oxygen or air. The additional diluents used can be noble gases, nitrogen, $CO_2$ or steam. These gases can be used in amounts of up to 10 moles, preferably of 4 to 10 moles, in particular of 4 to 7 moles per mole of alkylaromatic.

The pressure under which the reaction is carried out is generally within a range of 0.5–20 bar, preferably 0.5–3 bar, in particular 1 to 2 bar.

The zirconium phosphate catalyst has a stable long-term behavior with conversions of 40–70% at styrene selectivities of 80 to 95%. The catalyst is regenerated after a relatively long operating period through only incomplete burning-off, preferably at 400°–540° C., of carbon-containing deposits by means of oxygen or gases containing molecular oxygen. Regeneration is complete when the deposition on the catalyst has gone down to 7–15% by weight of carbon-containing deposits.

The examples which follow are intended to illustrate the invention in more detail but not to restrict it in any way.

EXAMPLE 1

Quantities of 0.5 M zirconium chloride solution and 3 M orthophosphoric acid were added together which were such that the atomic ratio of zirconium to phosphorus was 1:2. The resulting gel-like zirconium phosphate was added in an amount of 100 g to an excess, at least 1 liter, of 12 M orthophosphoric acid, and the resulting mixture was heated under reflux up to the boil with stirring for 12 hours. Thereafter, the zirconium phosphate was left for a further 38 hours in this strong phosphoric acid.

The resulting crystalline zirconium phosphate was washed with $H_2O$ until the $H_2O$ draining off had a pH of 3–4.

The material was dried for 24 hours in an air stream at a temperature of 120° C.

Two samples of catalyst, namely Zr-P-(1) and Zr-P-(3), were prepared in accordance with these instructions.

The use of only ⅓ of the amount of 12 M orthophosphoric acid but otherwise the same treatment as indicated above produced catalyst Zr-P-(2).

The activities of the catalyst were investigated on an integral micro-reactor. The latter can have, for example, a height of packing of 100 mm and a diameter of 12 mm. An integral micro-reactor of this type can also be used in the remaining examples. The amount of catalyst used was in each case 11 cm³. Screened material of particle size 0.63–1 mm was used. The reaction temperature was set at 450° C. The other operating conditions and experimental results obtained by means of the three samples of catalyst are shown in the table below. In that table, and in the following examples, RT denotes residence time, C denotes conversion, S denotes selectivity and EB denotes ethylbenzene.

| RT [s] | $EB/N_2$ [mole/mole] | $EB/O_2$ [mole/mole] | Zr—P—(1) C [%] | Zr—P—(1) S [%] | Zr—P—(2) C [%] | Zr—P—(2) S [%] | Zr—P—(3) C [%] | Zr—P—(3) S [%] |
|---|---|---|---|---|---|---|---|---|
| 0.71 | 1/7 | 1/1 | 39.8 | 86.1 | 9.5 | 82.1 | 37.0 | 89.1 |
| 1.5 | 1/7 | 1/0.7 | 39.2 | 86.4 | 16.3 | 76.2 | 40.6 | 89.1 |

The results show the very strong influence of the phosphoric acid treatment on catalyst activity.

EXAMPLE 2

To demonstrate the particularly favorable product spectrum obtained by means of the zirconium phosphate catalysts, the results of two performed experiments are shown. In experiment A, pure ethylbenzene (EB) was used as starting hydrocarbon. The RT of the reactants was 0.71 [s].

In experiment B, an equimolar ethylbenzene/styrene mixture was used (RT likewise being 0.71 [s]). The catalyst used was sample Zr-P-(1) which was used in the same amount as in Example 1. Oxygen and $N_2$ (as inert material) were added in an amount which was such that the molar ratios of $HC/O_2 = 1/1$ and $HC/N_2 = 1/7$ were produced (HC = hydrocarbons = Eb plus styrene).

The following results table shows that the only by-products observed in relatively large amounts were amounts were CO and $CO_2$, while toluene and benzene (indicated in the table as o.HC = other hydrocarbons) were found only in traces.

| | MOLE % | | | | | | | | |
|---|---|---|---|---|---|---|---|---|---|
| Experiment | CO | $CO_2$ | EB | STYRENE | $O_2$ | $H_2O$ | o.HC | C [%] | S [%] |
| A | 6.09 | 12.50 | 24.46 | 15.46 | 12.04 | 29.40 | 0.05 | 42.7 | 84.8 |
| B | 6.19 | 10.79 | 20.55 | 37.39 | 8.66 | 16.41 | 0.02 | 31.42 | 78.8 |

Example B also shows at the same time that still high selectivities can be obtained when reacting a mixture having a high styrene content. This is particularly important when consumed oxygen is to be replaced in an industrial reactor by intermediate feeding-in of additional oxygen whereby further reaction then comes possible. To clarify this issue, a theoretical model for a multi-stage reactor with additional oxygen between the reactor stages was computed on the basis of kinetic equations. The projection was carried out for a production level of 70,000 tonnes per annum of styrene and use of the catalyst Zr-P-(1). At the entry of the 1st reactor stage $O_2$ is added in the form of air. Between the reactor stages pur oxygen is added so that the $EB/O_2$ ratios shown in the table below are produced. The table shows the conversions and selectivities which can be obtained in each reactor stage.

| Reactor stage | Length [m] | Oxygen at entry $EB/O_2$ [mole/mole] | $T_{IN}$ [°C.] | $T_{OUT}$ [°C.] | C [%] | S [%] |
|---|---|---|---|---|---|---|
| 1 | 0.57 | 1/1 | 400 | 480 | 22 | 83 |
| 2 | 0.68 | 1/1 | 415 | 480 | 39.3 | 82.5 |
| 3 | 0.65 | 1/1.5 | 425 | 480 | 53.5 | 81 |
| 4 | 1.44 | 1/1.5 | 425 | 480 | 66.6 | 79.4 |
| 5 | 1.66 | 1/2 | 425 | 442 | 71 | 79.1 |

$T_{In}$ denotes the temperature of the mixture on entry, and $T_{Out}$ denotes the temperature of the mixture on leaving the particular stage.

EXAMPLE 3

To prepare a zirconium phosphate catalyst doped with Cs ions, 50 ml of 0.2 M $Cs_2SO_4$ solution were added to 400 ml of the washed gel-like zirconium phosphate and the mixture was stirred for 32 hours. Further treatment was as indicated in Example 1.

An activity investigation on the integral microreactor (amount of catalyst 11 cm³) produced the conversions and selectivities indicated in the table. The reaction temperature in the experiments was 450° C.

| RT [s] | EB/N$_2$ [mole/mole] | EB/O$_2$ [mole/mole] | C [%] | S [%] |
|---|---|---|---|---|
| 0.71 | 1/7 | 1/1 | 36.9 | 89.9 |
| 1.5 | 1/7 | 1/0.7 | 40.2 | 90.7 |

EXAMPLE 4

Experiments to investigate the long-term behavior were carried out on the catalyst Zr-P-(1) using different residence times (A:2.47 s, B:0.71 s) of the reactants on the catalyst. The reaction temperature in both experiments was 450° C. The molar ratios set were EB/O$_2$=1/1 and EB/inert 1/7.

The results are shown in the following table.

| Long-term experiment A | | | Long-term experiment B | | |
|---|---|---|---|---|---|
| Duration of experiment [h] | Conversion [%] | Selectivity [%] | Duration of experiment [h] | Conversion [%] | Selectivity [%] |
| 0.3 | 63.4 | 83.2 | 1.0 | 28.0 | 87.4 |
| 1.0 | 67.2 | 91.2 | 8.0 | 46.0 | 88.3 |
| 1.5 | 65.2 | 90.7 | 9.5 | 48.0 | 87.1 |
| 1.8 | 61.1 | 90.0 | 13.5 | 50.1 | 85.0 |
| 2.5 | 58.1 | 86.2 | 18.8 | 50.4 | 84.7 |
| 5.0 | 51.2 | 84.0 | 26.1 | 49.8 | 83.6 |
| 9.5 | 52.2 | 83.0 | 33.6 | 48.9 | 82.5 |
| 16 | 50.4 | 80 | 37.8 | 47.9 | 81.7 |
| 24 | 50.3 | 80.5 | 41.0 | 48.1 | 81.2 |
| 48 | 50.2 | 80.4 | 80 | 47.9 | 80.8 |

The data indicated in the table show that there is an activity maximum after a short operating period. On operating for longer periods an almost constant activity value is then obtained. It was possible to maintain this activity for a period of 160 hours-200 hours. Only then did the lowering of the activity necessitate regeneration of the catalyst. It was possible to effect this by simply passing over N$_2$/O$_2$ in the form of air at a temperature of 450° C. In this step, it was not necessary to burn off the carbonization products until the catalyst was completely carbon-free. It was sufficient to regenerate down to a deposition on the catalyst of 7–15% by weight of carbon-containing deposits. This means that the regenerating period is considerably shortened from the usual 6.5 hours to about 1.5 hours. After a regeneration of this type, as was necessary after about 160 hours in the long-term experiment B, conversions of 48% and selectivities of 81.5% were then again obtainable. The catalyst Zr-P-(1) was used for a total of 3,500 hours in the integral micro-reactor. During this period the catalyst was regenerated about 30 times and even toward the end of the investigation period it was possible to obtain experimental results as had already been obtained at the starting.

EXAMPLE 5

To investigate the effect of the concentration of the inert material, experiments were carried out using various EB/N$_2$ ratios. Again catalyst Zr-P-(1) (amount: 11 cm$^3$) was used at a temperature of 450° C. in the integral micro-reactor. On entry into the reactor oxygen was added in an amount such that a EB/O$_2$ ratio of 1.1 was produced. Ethylbenzene was added at a rate of 3.2 g/h. The results are shown in the following table.

| EB/N$_2$ [mole/mole] | C [%] | S [%] |
|---|---|---|
| 1/4 | 60.0 | 70.0 |
| 1/7 | 53.0 | 75.0 |
| 1/10 | 52.5 | 78.0 |

EXAMPLE 6

The influence of the concentration of oxygen was investigated at a content of inert material (inert material N$_2$) of EB/N$_2$=1/7. In these experiments, ethylbenzene was added at a rate of 2.9 g/h (catalyst Zr-P-(1): 11 cm$^3$). The results of these experiments have been collated in the following table.

| T [°C.] | EB/O$_2$ [mole/mole] | C [%] | S [%] |
|---|---|---|---|
| 430 | 1/0 | 0 | — |
| 430 | 1/0.5 | 40.5 | 95.0 |
| 430 | 1/1.0 | 50.3 | 88.9 |
| 430 | 1/1.5 | 58.1 | 84.1 |
| 430 | 1/2.0 | 60.3 | 81.8 |
| 435 | 1/2.3 | 61.6 | 81.1 |
| 460 | 1/2.7 | 68.8 | 76.2 |
| 500 | 1/3.0 | 76.5 | 70.4 |
| 540 | 1/3.2 | 79.4 | 64.0 |

EXAMPLE 7

To investigate the influence of the reaction temperature, experiments were carried out at differing temperature but otherwise identical reaction conditions. Catalyst Zr-P-(1) was used in an amount of 11 cm$^3$. Ethylbenzene was added at a rate of 11.1 g/h. The molar feed ratios EB/N$_2$ and EB/O$_2$ were set at the values ¼ and 1/1 respectively (N$_2$ and O$_2$ in the form of air). The conversions and selectivities obtained were as shown in the following table.

| T [°C.] | C [%] | S [%] |
|---|---|---|
| 400 | 21.1 | 86.2 |
| 420 | 26.3 | 84.4 |
| 430 | 29.8 | 84.8 |
| 450 | 39.3 | 85.4 |
| 460 | 42.4 | 84.0 |
| 485 | 48.6 | 84.1 |
| 500 | 50.1 | 83.5 |

We claim:

1. A process for oxidatively dehydrogenating ethylbenzene to prepare styrene, which process comprises reacting ethylbenzene in the vapor phase with oxygen at a temperature above 350° C. in the presence of a crystalline zirconium phosphate catalyst capable of ion exchange, said zirconium phosphate catalysts having been precipitated in a gel-like form from a zirconium salt solution by the addition of an excess of phosphate ions, impregnated with at least 1 liter of an at least 10 M orthophosphoric acid per 100 g of zirconium phosphate gel, filtered off from excess phosphoric acid, washed with water until the water draining off has a pH of 2 to 3 and dried at 120° to 250° C.

2. The process as claimed in claim 1, wherein a mixture of an oxygen-containing gas and ethylbenzene is passed over the catalyst at a temperature of 350° C.–550° C. and a residence time of 0.5 to 5 grams of gas mixture per gram of catalyst per hour.

3. The process as claimed in claim 2, wherein the ethylbenzene is diluted with an up to 10-fold amount of inert gas.

4. The process as claimed in claim 1, wherein the temperature is about 380° C. to 530° C.

5. The process as claimed in claim 1, wherein the molar ratio of oxygen ethylbenzene is 0.5:1 to 2:1.

6. The process as claimed in claim 1, wherein the catalyst is subjected to an impregnating period of 10 to 14 hours at about the boiling point and to 30-40 hours at room temperature and to a drying period of 24-48 hours.

7. The process as claimed in claim 1, wherein Cs ions are added before the impregnating step and drying step.

8. The process as claimed in claim 1, wherein the catalyst has a surface area of 10-50 m²/g.

9. The process as claimed in claim 1, wherein the regeneration of the catalyst, when necessary, is carried out by incompletely burning off the carbon-containing deposits at 400°-540° C. down to a residual content of 7-15% by weight by means of oxygen or gases which contain molecular oxygen.

10. The process as claimed in claim 1, wherein the catalyst further contains ions of an element from the group Ia, IIa, IVb, Vb, VIb, VIIb or VIII of the periodic system of the elements.

11. The process as claimed in claim 10, wherein the ions are contained in the catalyst in a concentration of 1-20% by weight.

12. The process as claimed in claim 10, wherein the ions are taken from the group of K, Cs, Mg, Ba, Cr, Mn, Fe or Ni ions.

13. The process as claimed in claim 10, wherein the ions are taken from the group of K, Cs, Ba, Fe, or Ni ions.

14. The process as claimed in claim 10, wherein the ions are taken from the group of K, Cs, Mg, Cr, Mn, Fe or Ni ions.

* * * * *

UNITED STATES PATENT AND TRADEMARK OFFICE
CERTIFICATE OF CORRECTION

PATENT NO. : 4,400,568
DATED : August 23, 1983
INVENTOR(S) : Hofmann et al.

It is certified that error appears in the above-identified patent and that said Letters Patent is hereby corrected as shown below:

Column 1, line 62, change "gas mixture per gram of catalyst" to --catalyst per gram of gas mixture--.
Column 2, line 15, change "or" to --of--.
        line 34, after "values" insert --of $PO_4$ to Zr--;
        line 35, change "2" to --2:1--, and change "3" to --3:1--.

Column 3, line 24, change "acid, and the" to --acid. For this example, 1 liter of 12 M orthophosphoric acid was used. The--.
        line 59, change "86.4" to --73.0--.
Claim 2, lines 4 and 5, change "gas mixture per gram of catalyst" to --catalyst per gram of gas mixture--.

Column 3, line 31, change "3-4" to --2-3--.

Signed and Sealed this

*Twenty-first* Day of *May 1985*

[SEAL]

*Attest:*

DONALD J. QUIGG

*Attesting Officer*     *Acting Commissioner of Patents and Trademarks*